United States Patent
Cong et al.

(10) Patent No.: US 6,544,396 B1
(45) Date of Patent: Apr. 8, 2003

(54) MULTIPLEXED CAPILLARY ELECTROPHORESIS SYSTEM

(75) Inventors: Peijun Cong, San Jose, CA (US); Robert D. Doolen, Sunnyvale, CA (US)

(73) Assignee: Symyx Technologies, Inc., Santa Clara, CA (US)

(*) Notice: Subject to any disclaimer, the term of this patent is extended or adjusted under 35 U.S.C. 154(b) by 328 days.

(21) Appl. No.: 09/621,890

(22) Filed: Jul. 20, 2000

(51) Int. Cl.[7] ............. C02F 1/40; C02F 11/00; C25B 11/00; C25B 13/00; C25B 9/00; G01N 27/27; G01N 27/403; G01N 27/453

(52) U.S. Cl. ............................................. 204/601

(58) Field of Search ............................. 204/601

(56) References Cited

U.S. PATENT DOCUMENTS

| | | | |
|---|---|---|---|
| 3,655,980 A | 4/1972 | Bossen ............ 250/83.3 D |
| 4,172,227 A | 10/1979 | Tyrer et al. ............ 250/461 B |
| 4,375,163 A | 3/1983 | Yang .................. 73/61.1 C |
| 4,576,477 A | 3/1986 | Corbet et al. ............ 356/39 |
| 4,618,769 A | 10/1986 | Johnson et al. ........... 250/338 |
| 4,747,686 A | 5/1988 | Sato ...................... 356/72 |
| 5,003,488 A | 3/1991 | Hardy .................... 364/509 |
| 5,021,646 A | * 6/1991 | Weinberger et al. ....... 204/603 |
| 5,045,172 A | 9/1991 | Guzman .............. 204/299 R |
| 5,066,382 A | 11/1991 | Weinberger et al. ... 204/299 R |
| 5,085,757 A | 2/1992 | Karger et al. ......... 204/299 R |
| 5,122,253 A | * 6/1992 | Christianson ............ 204/601 |
| 5,164,064 A | * 11/1992 | Dill et al. ............... 204/601 |
| 5,183,101 A | * 2/1993 | Penaluna et al. ........ 165/104.33 |
| 5,198,091 A | * 3/1993 | Burolla et al. ........... 204/601 |
| 5,239,360 A | 8/1993 | Moring et al. ............ 356/344 |
| 5,274,240 A | 12/1993 | Mathies et al. .......... 250/458.1 |
| 5,303,021 A | 4/1994 | Kita ...................... 356/72 |
| 5,312,535 A | 5/1994 | Waska et al. ......... 204/299 R |
| 5,324,401 A | 6/1994 | Yeung et al. ............ 204/180.1 |
| 5,413,686 A | 5/1995 | Klein et al. ........... 204/299 R |
| 5,439,578 A | 8/1995 | Dovichi et al. ........ 204/299 R |
| 5,488,240 A | 1/1996 | Hlousek et al. ........ 250/231.16 |
| 5,582,705 A | 12/1996 | Yeung et al. ............ 204/603 |
| 5,611,903 A | 3/1997 | Janssens et al. .......... 204/454 |
| 5,695,626 A | 12/1997 | Yeung et al. ............ 204/605 |
| 5,730,850 A | 3/1998 | Kambara et al. .......... 204/603 |
| 5,741,411 A | 4/1998 | Yeung et al. ............ 204/452 |
| 5,885,430 A | * 3/1999 | Kernan et al. ............ 204/451 |
| 5,900,934 A | 5/1999 | Gilby et al. .............. 356/344 |
| 6,027,627 A | * 2/2000 | Li et al. ................. 204/451 |
| 6,063,251 A | * 5/2000 | Kane et al. ............. 204/601 |
| 6,103,081 A | * 8/2000 | Morris et al. ............ 204/451 |

FOREIGN PATENT DOCUMENTS

WO 99/42819 8/1999

OTHER PUBLICATIONS

Culbertson, C.T. et al., "Lowering The UV Absorbance Detection Limit In Capillary Zone Electrophoresis Using A Single Linear Photodiode Array Detector", Anal. Chem., vol. 70, pp. 2629–2638, 1998.
Gong, Xiaoyi et al., "An Absorption Detection Approach For Multiplexed Capillary Electrophoresis Using A Linear Photodiode Array", Analytical Chemistry, pp. A–H, 1999.
Product Catalog, "Swagelok® BMS Series Bellows Sealed Metering Valves", Nupro Company, Feb. 1997.
Product Catalog, "Swagelok® Ultra–High–Purity Diaphragm Valve; DA Series", Nupro Company, May 1998.
Product Bulletin 640/641, "Electronic Pressure Controllers, 640 Series", MKS Instruments, Inc., Jul. 1995.

* cited by examiner

Primary Examiner—T. Tung
Assistant Examiner—Jennine Brown
(74) Attorney, Agent, or Firm—Senniger, Powers, Leavitt & Roedel

(57) ABSTRACT

A multiplexed capillary electrophoresis system with cooling sufficient to prevent overheating during chiral separation. The system includes a thermally insulated enclosure enclosing a bundle of capillary tubes, a light source and photodetector. A heat transfer system is provided for cooling closely spaced portions and spread apart portions of the capillary tubes to an extent sufficient to prevent overheating of the tubes and contents thereof due to the heat generated during chiral separation.

23 Claims, 12 Drawing Sheets

MULTIPLEXED CAPILLARY ELECTROPHORESIS SYSTEM

BACKGROUND OF THE INVENTION

This invention is generally in the field of capillary electrophoresis, and relates particularly to a system for and a method of cooling the capillaries of a multiplexed or "parallel" capillary electrophoresis system.

Capillary electrophoresis (CE) is a chemical separation technique involving the use of one or more capillary tubes. Parallel CE, a recently developed technique using many parallel capillary tubes, is growing in popularity since this technology allows multiple samples to be analyzed quickly and efficiently. This is particularly advantageous in combinatorial chemistry where many hundreds and even thousands of samples are analyzed over a short period of time. Parallel CE involves the use of a "bundle" of capillary tubes, e.g., 96 such tubes. A chemical sample to be analyzed is loaded in each tube, and a high voltage is applied to the tube, causing the components of the sample to migrate in the tube at different speeds, thereby causing separation of the components which can then be analyzed by conventional light absorption or other techniques. Reference may be made to the following patents and publications for a more detailed description of CE, including parallel CE, and various analytical techniques used in CE: U.S. Pat. Nos. 5,900,934, 5,324,401, 5,312,535, 5,303,021, 5,239,360; C. Culbertson et al., Analytical Chemistry, 70, 2629–2638 (1998); and X. Gong et al., Analytical Chemistry, 71(2a); 4989–4996 (1999). None of these publications disclose the use of parallel CE to achieve chiral separation.

The electrical current passing through the parallel capillary tubes of a CE system can generate a substantial amount of heat, particularly where high voltages and electrical currents are used to achieve the separation of the samples, as in a chiral separation process using chiral buffers. If not dissipated, this heat can cause the formation of bubbles in the samples, sparking, and other undesirable results having an adverse affect on separation and analysis. Therefore, there is a need for a system for effectively cooling such tubes.

SUMMARY OF THE INVENTION

Among the several objects of this invention may be noted the provision of a multiplexed (parallel) CE system for effecting chiral separation at higher throughput; the provision of such a system with cooling apparatus sufficient to prevent overheating of the capillary tubes and contents thereof during chiral separation and other processes generating substantial heat; the provision of such a system and cooling apparatus which has no adverse affect on the separation and/or analytical process; the provision of such cooling apparatus which is adjustable to various cooling temperatures; the provision of such cooling apparatus which can be configured to remove a desired amount of heat; the provision of such apparatus which is safe to use.

In general, this invention is directed to a multiplexed capillary electrophoresis system with cooling sufficient to prevent overheating during separation. The system comprises a bundle of capillary tubes having inlet end portions spaced apart for loading of fluid samples to be analyzed into the tubes, outlet end portions for exit of the fluid samples from the tubes, and intermediate portions between the inlet and outlet end portions arranged in a generally planar array in which the intermediate portions extend side-by-side in closely spaced generally parallel relation. The system includes a power source adapted for applying a potential difference between the inlet end portions and the outlet end portions to cause an electrical current to flow through the contents of the capillary tubes at a level sufficient to cause separation in the fluid samples, the current generating heat in the tubes and the contents thereof. A light source is provided for directing light to pass through the generally planar array of intermediate portions of the capillary tubes, and a photodetector is provided for receiving light passing through said array. A thermally insulated enclosure encloses the bundle of capillary tubes, light source and photodetector. The system further comprises a heat transfer system for cooling the array and the inlet end portions of the capillary tubes to an extent sufficient to prevent overheating of the tubes and contents thereof due to said heat. In the preferred embodiment, this system includes a first heat transfer mechanism for cooling the array of closely spaced intermediate portions of the capillary tubes, and a second heat transfer mechanism for cooling the spaced apart inlet end portions of the capillary tubes.

In another aspect, this invention is directed to a multiplexed capillary electrophoresis system comprising a bundle of capillary tubes having inlet end portions positioned for loading of fluid samples to be analyzed into the tubes, outlet end portions for exit of said samples from the tubes, and intermediate portions between the inlet and outlet end portions arranged in an array in which the intermediate portions extend side-by-side in closely spaced generally parallel relation. The system includes a power source for applying a potential difference between the inlet end portions and the outlet end portions to cause an electrical current to flow through the contents of the capillary tubes at a level sufficient to cause separation in said fluid samples. A light source is provided for directing light to pass through the array of intermediate portions of the capillary tubes, and a photodetector receives light passing through the array. A heat transfer system is provided for cooling the array and the inlet end portions of the capillary tubes to an extent sufficient to prevent overheating of the tubes and contents thereof due to heat generated during separation. A thermally insulated enclosure encloses the bundle of capillary tubes, light source, photodetector, and said heat transfer system.

In one embodiment, a multiplexed capillary electrophoresis system of this invention comprises a conduction heat transfer mechanism for cooling the aforementioned array of closely spaced intermediate portions of the capillary tubes. The conduction heat transfer mechanism comprises a body of thermally conductive material having a length, a width, and a cooling face adapted to extend across substantially the entire width of the bundle for cooling the capillaries of the bundle. The cooling face is electrically insulated from the capillaries. A window is provided in the body for exposing the array.

The present invention is also directed to a method of preventing overheating of a bundle of capillary tubes during a multiplexed capillary electrophoresis process for substantially concurrently effecting separation in multiple fluid samples. The method comprises the steps of mounting a bundle of capillary tubes in an insulated enclosure so that inlet end portions of the tubes are spaced apart for loading of the fluid samples into the tubes and intermediate portions of the tubes are arranged in a generally planar array in which the intermediate portions extend side-by-side in closely spaced generally parallel relation. The fluid samples are loaded into the inlet end portions of the tubes, after which an electrical current is caused to flow through the contents of the capillary tubes at a level sufficient to cause separation in the fluid samples, the current generating heat in the tubes and the contents thereof. The method involves analyzing one or more properties of the fluid samples as they flow through the array of intermediate portions of the capillary tubes. The array and inlet end portions of the capillary tubes are cooled to an extent sufficient to prevent overheating of the tubes and contents thereof due to said heat. In the preferred embodiment, the closely spaced array of tubes is cooled by using a first heat transfer mechanism, and the spaced apart inlet end portions of the capillary tubes are cooled by using a second heat transfer mechanism.

BRIEF DESCRIPTION OF THE DRAWINGS

Corresponding parts are designated by corresponding reference numbers throughout the several views of the drawings.

DETAILED DESCRIPTION OF THE PREFERRED EMBODIMENT

Figure 1:
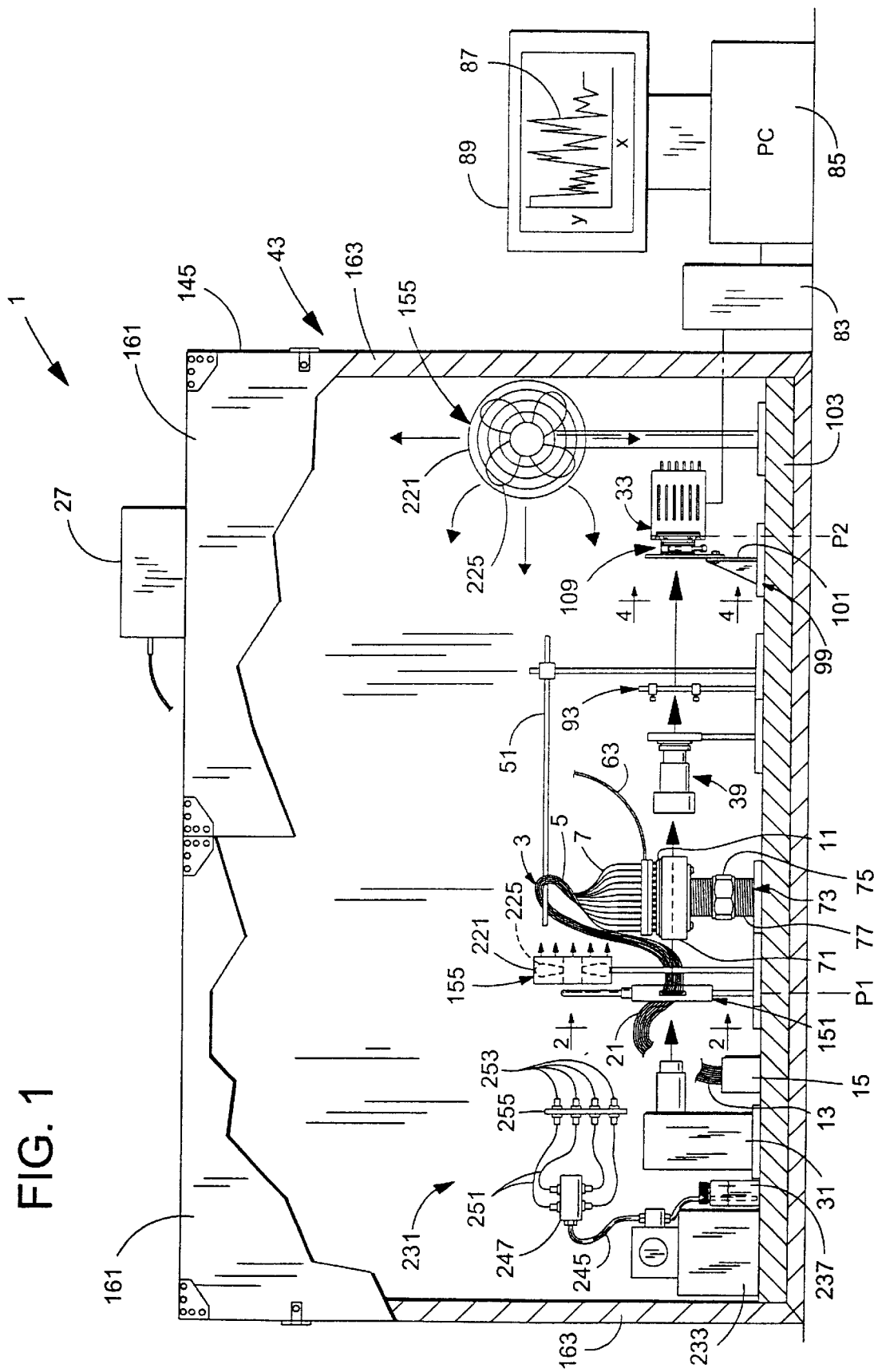
FIG. 1 is a schematic view of a capillary electrophoresis system with cooling apparatus for preventing overheating of the capillary tubes during a chiral separation process.
Figure 2:
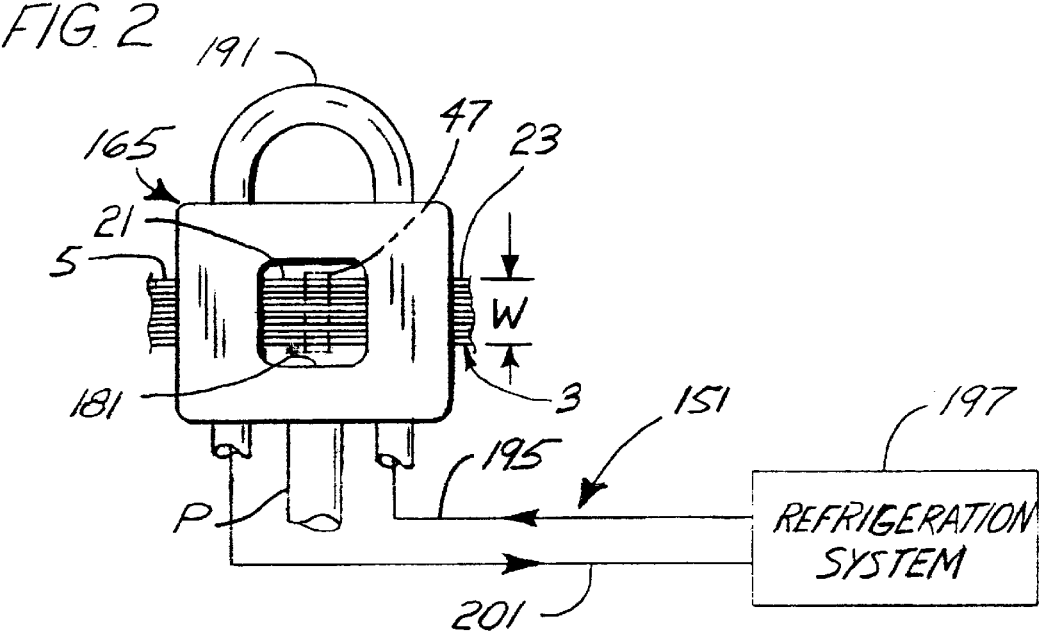
FIG. 2 is an enlarged view along lines 2—2 of FIG. 1 showing a conduction cooling device for cooling an array of closely spaced parallel capillary tubes.
Figure 10:
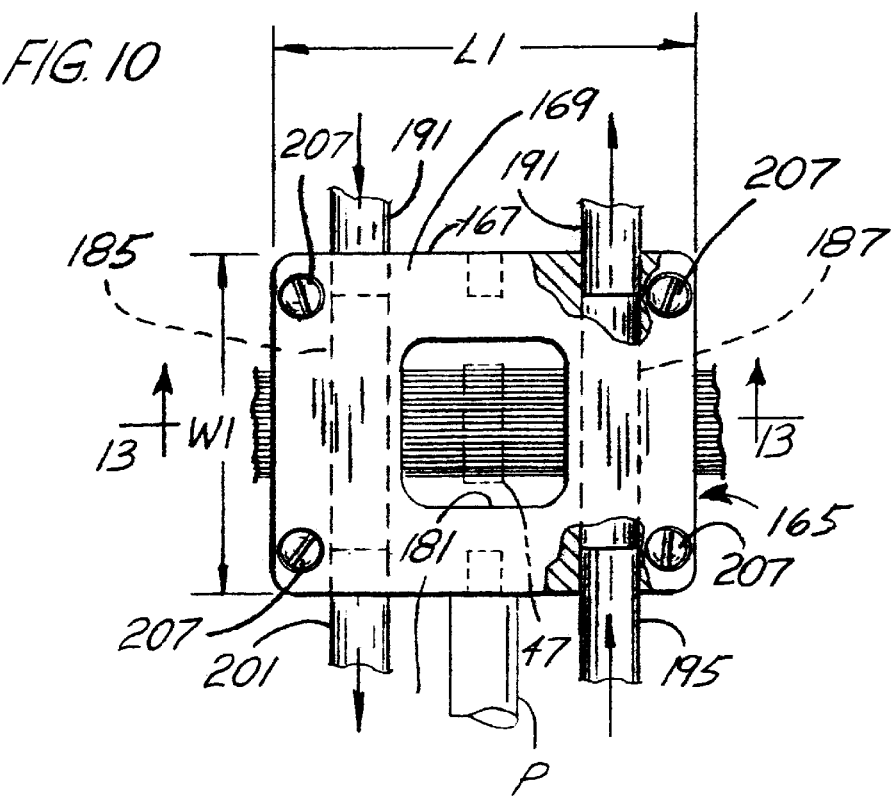
FIG. 10 is a front view of certain components of the cooling device of FIG. 2, including a cooling body.

Referring now to the drawings, FIG. 1 shows a multiplexed (parallel) capillary electrophoresis (CE) system, generally indicated at 1, for separating and analyzing the components of multiple chemical samples. The system comprises a bundle 3 of capillary tubes 5 having inlet end portions 7 spaced apart (e.g., spread out in a fanned formation) for loading of fluid samples to be analyzed from individual wells 9 (FIG. 3) in a microtiter plate 11 into the tubes, outlet end portions 13 for exit of the fluid samples from the tubes into a waste receptacle 15, and intermediate portions 21 between the inlet and outlet portions arranged in a generally planar, ribbon-like array 23 (FIG. 2) in which the intermediate portions extend side-by-side in closely spaced generally parallel relation in a first plane P1. The system also includes a power source 27 for applying a potential (voltage) difference between the inlet end portions 7 and the outlet end portions 13 to cause an electrical current to flow through the contents of the capillary tubes 5, a light source 31 for emitting light to pass through the closely spaced array 23 of intermediate portions 21 of the capillary tubes, and a photodetector generally designated 33 comprising a linear array 34 of photodetector elements (35 in FIGS. 8 and 9) in a second plane P2 generally parallel to the first plane P1 for receiving light passing through the planar array of intermediate portions of the capillary tubes. Light passing through the tubes 5 is imaged on the photodetector 33 by an imaging lens, generally designated 39. In accordance with this invention, the system also includes a cooling system, generally indicated at 43, for dissipating the large quantities of heat generated in the capillary tubes 5 and contents thereof during a high-heat separation process, such as a chiral separation process.

More specifically, the capillary bundle 3 may comprise a series of 96 capillary tubes 5, although this number may vary. Each tube 5 is of relatively small diameter (e.g., 75 microns ID; 150 microns OD) and of a suitable electrically nonconductive material, such as fused silica so that high voltages can be applied across tube without generating excessive heat. The tubes 5 may have a polyimide coating which is removed by a laser beam, for example, in an area extending across the planar array 23 of intermediate portions 21 of the capillary tubes, thereby forming what may be referred to as a detection window (47 in FIG. 2) which is transparent or translucent so that light from the light source 31 can pass through the walls of the tubes at this location. Alternatively, the tubes can be transparent or translucent along their entire lengths, in which case no coating removal is necessary. The bundle 3 is of any appropriate length (e.g., 10 cm–2 m). At the detection window 47 the bundle 3 has a width, designated W in FIG. 2, in a direction generally perpendicular to its length. As illustrated in FIG. 1, the bundle 3 may be supported above its inlet end portions 7 by a suitable support device 51. The capillary tubes 5 of the bundle 3 may be held in the aforementioned planar array 23 by any suitable means, such as by strips of adhesive tape (not shown) extending across the array on opposite sides of the detection window 47.

Figure 3:
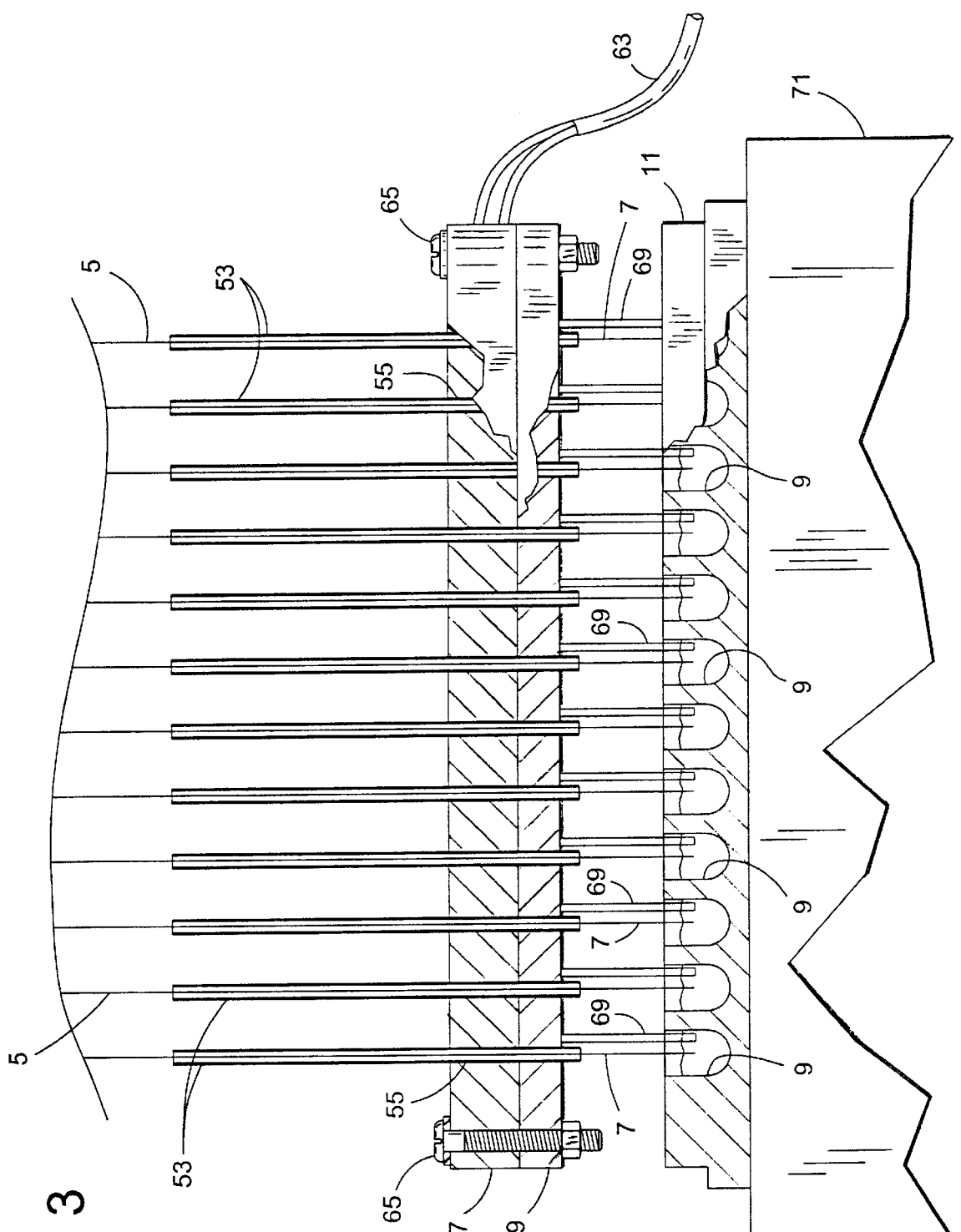
FIG. 3 is an enlarged sectional view of capillary tubes extending down through power plates into the wells of a microtiter plate.

Referring to FIG. 3, the inlet end portions 7 of the capillary tubes 5 extend through tubular sleeves 53 of electrical insulating material slidably received in holes 55 in a pair of upper and lower metal power plates 57, 59 connected to the power source 27 by suitable electrical cable 63. The two plates 57, 59 are secured together by fasteners 65. The inner end portions 7 of the capillary tubes 5 extend down beyond the sleeves 53 and into respective wells 9 in the microtiter plate 11 containing liquid samples of chemical compositions to be analyzed. Metal electrodes 69 are secured (e.g., brazed) to the bottom face of the lower power plate 59 and extend down into the wells 9 alongside the capillary tubes 5 for electrifying the contents of the wells when the power source 27 is activated. The power plates 57, 59 and electrodes 69 are preferably of copper or other suitable metal, and the lower plate 59 and electrodes are preferably gold plated to render them chemically inert or non-reactive. To effect chiral separation, substantially more (3–5 times more) current must be used than in non-chiral separations. For example, for a bundle of 96 capillary tubes, a total current of 1–20 milliamps at a voltage of 5,000–30,000 volts may be required to effect chiral separation. A suitable power source for this application is Model 105–30R, available from Bertan High Voltage Corporation located in Hicksville, N.Y.

The microtiter plate 11 is supported by a thick insulating block 71 of dielectric material which is movable up and down relative to the power plates 57, 59 by a linear actuator generally designated 73. The actuator 73 is operated by rotating a nut 75 relative to a screw shaft 77 in one direction to extend the actuator and thus raise the insulating block 71 and microtiter plate 11, and in the opposite direction to retract the actuator and thus lower the block and microtiter plate. Alternatively, the actuator can be a power (e.g., pneumatic) actuator with suitable controls.

The light source 31 may be of any suitable type, such as a deuterium or tungsten lamp or a 254-nm mercury lamp, emitting light having a certain wavelength (e.g., 200–800 nm and generalizable to other wavelengths) corresponding to the absorption band of the sample components of interest. The light is typically ultraviolet or visible light.

Figure 8:
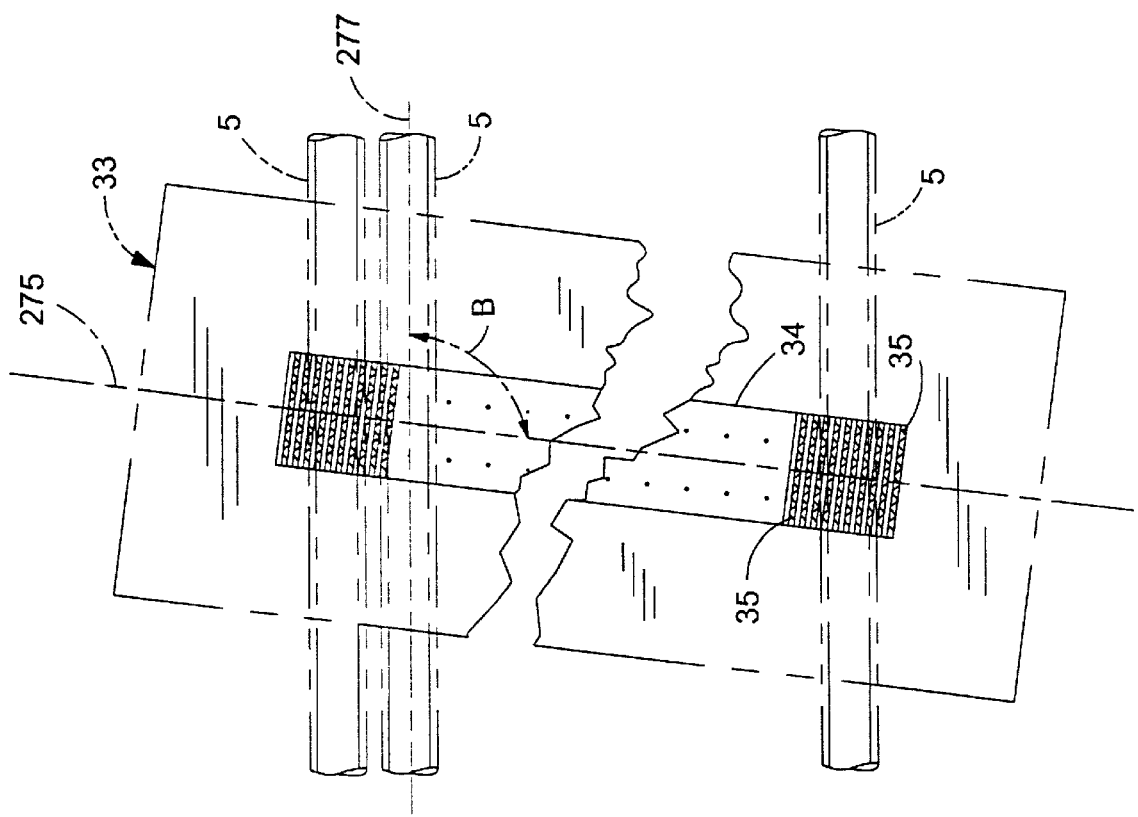
FIG. 8 is a view of a linear array of photodetector elements and an image of capillary tubes projected on the array, the linear array being skewed relative to the lengths of the tubes.
Figure 9:
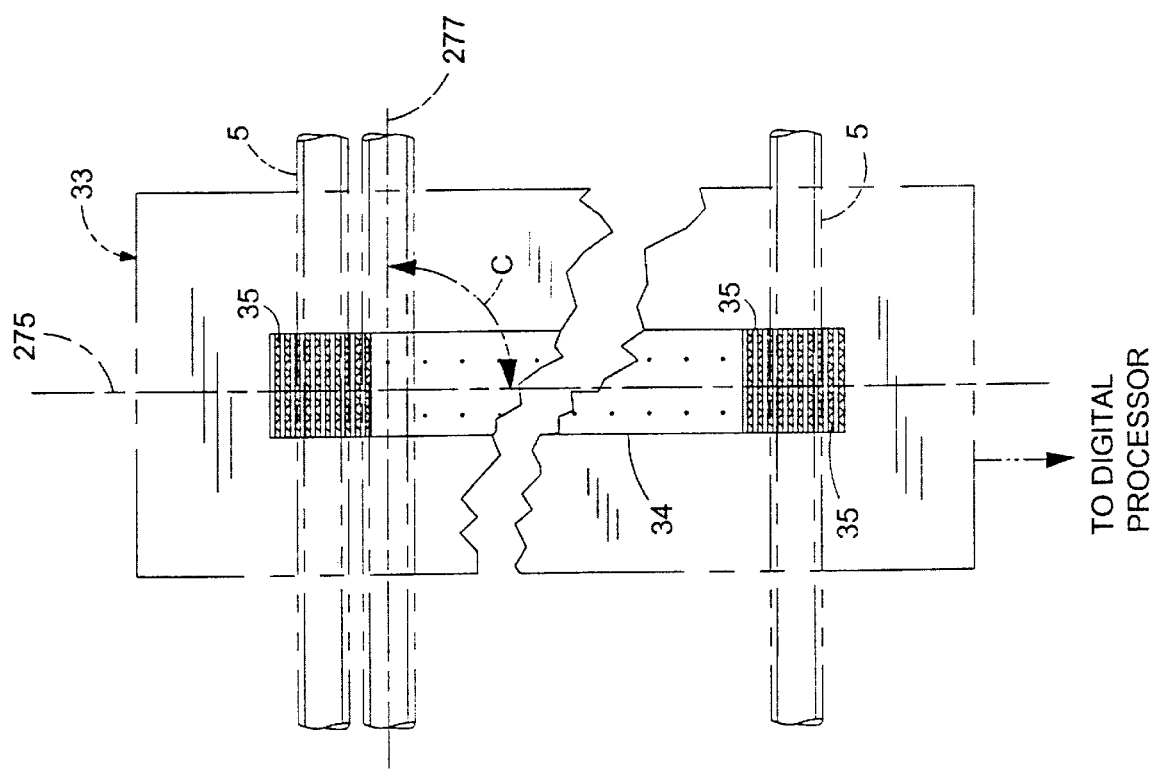
FIG. 9 is a view similar to FIG. 8 but showing the linear array rotated to a position generally perpendicular to the lengths of the tubes.

The photodetector 33 is of a conventional type, such as a photodiode device, having the aforementioned linear array 34 of photodetector elements 35 (FIGS. 8 and 9). These elements may be photodiodes, for example, arranged in one or more linear rows. For example, the photodetector 33 may be a model C5964 multichannel detector head by Hamamatsu incorporating a linear image sensor chip, a low-noise driver/amplifier circuit, and a temperature controller. In this example, the linear image sensor chip has 1024 diodes, each of which is 25 microns in width and 2500 microns height. Other types of photodetectors 33 can be used without departing from the scope of this invention. The photodetector elements 35 generate output signals which are then transmitted to a digital processor 83 (FIG. 1) and related equipment (e.g., a computer 85) for generating and displaying an electropherogram, i.e., a plot of light intensity versus time, as will be understood by those skilled in this field. This plot can then be evaluated to identify components of interest in the samples being analyzed. As shown in FIG. 1, the electropherogram 87 can be displayed on a screen 89 of the computer 85.

The imaging lens 39 may also be of conventional design, such as a quartz lens (Sodern; f.1.=94 mm; F=4.1) in combination with an interference filter 93 (Oriel) employed to define the absorption wavelength. The lens 39 is positioned between the detection window 47 and the photodetector 33 to receive light passing through the capillary tubes 5 and to image that light on the linear array 33 of photodetector elements 35. The image of the capillary tubes 5 projected by the lens 39 on the photodetector 33 may be an image 1.5 times actual size, for example.

Figure 4:
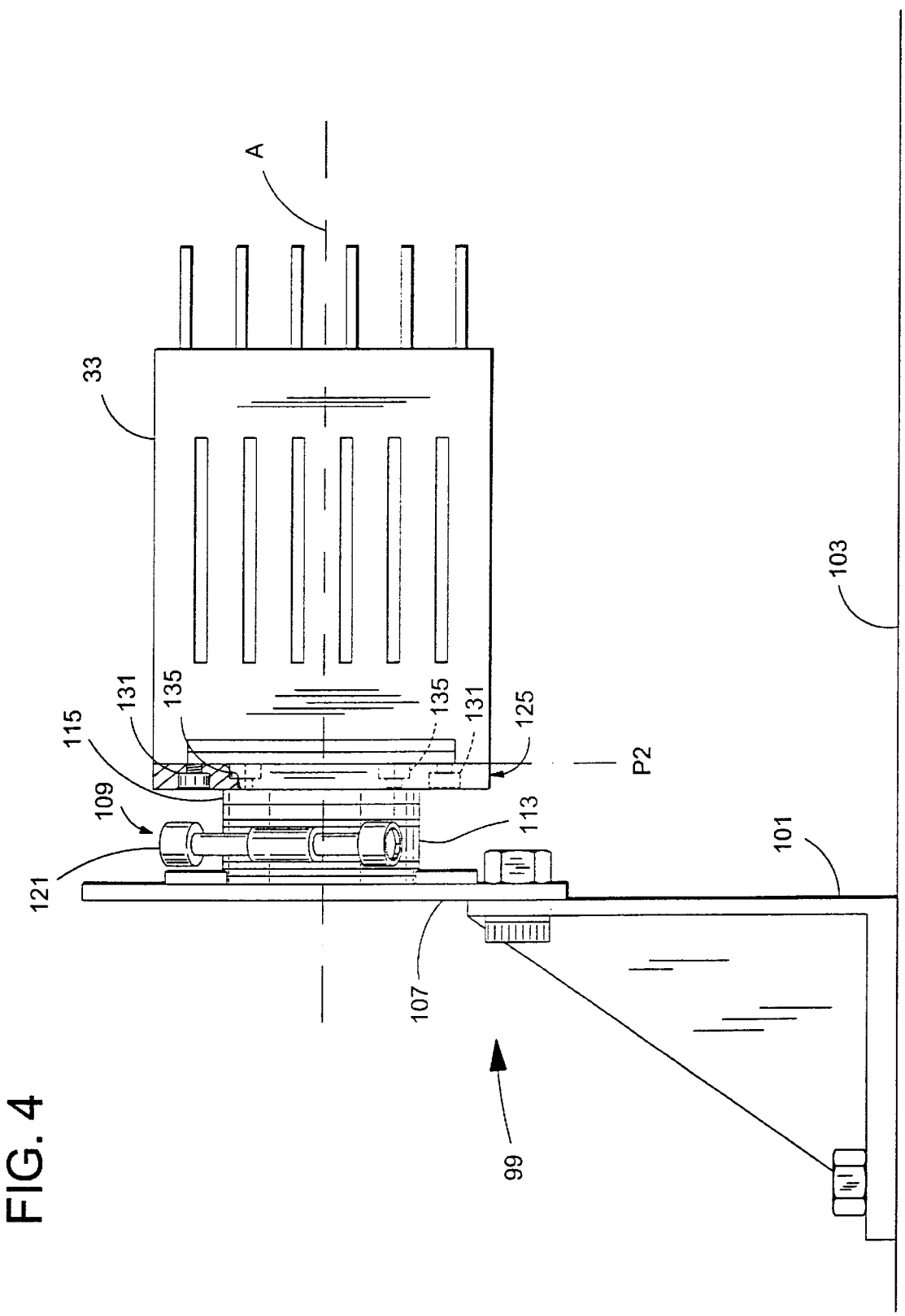
FIG. 4 is a side elevation of a photodetector mounted on a rotational stage.
Figure 5:
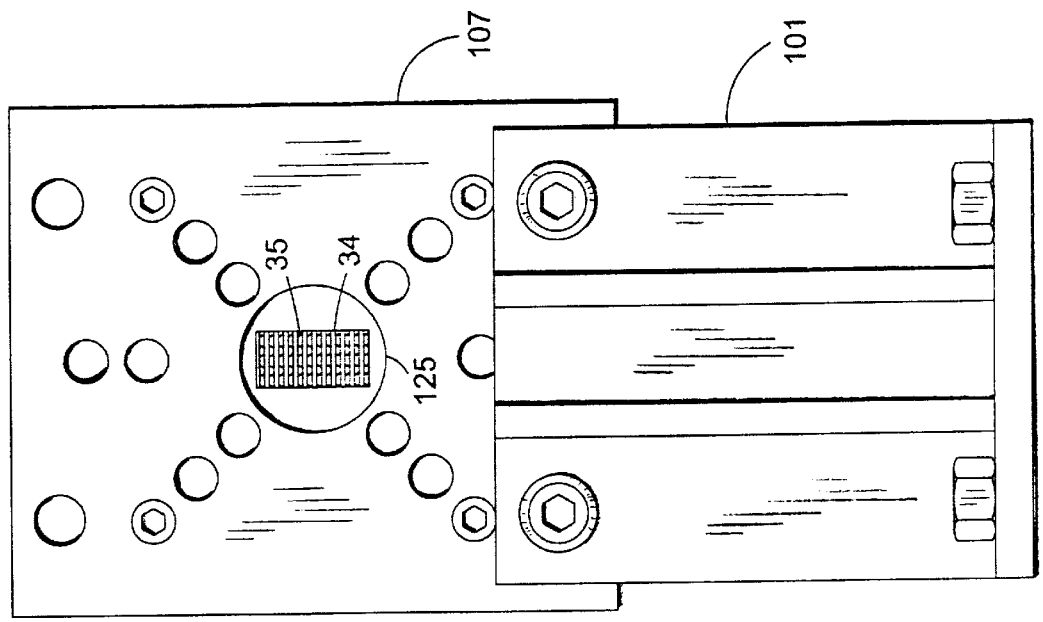
FIG. 5 is a front elevation of a mount for the rotational stage.

Referring to FIGS. 1 and 4, a mounting assembly, generally designated 99, is provided for mounting the photodetector 33 for rotation about a generally horizontal axis A. This assembly 99 comprises a bracket 101 attached to the floor 103 of an enclosure to be described later in detail, a vertical mounting plate 107 attached to the bracket and extending up from the bracket, and a rotational stage, generally designated 109, attached to the mounting plate. The rotational stage 109 comprises a stationary ring unit 113 attached to the mounting plate 107, and a rotatable ring unit 115 concentric with the stationary ring unit and rotatable relative thereto about the aforesaid horizontal axis A. The rotational stage 109 has a gross angular adjustment (e.g., a set screw arrangement not shown) whereby the rotatable ring unit 115 can be quickly rotated to an approximate angular position, and a fine angular adjustment (e.g., a screw-type adjustment 121) whereby the angular position of the rotatable ring unit can be slowly moved to a precise position, the angular adjustment mechanism then functioning to hold or maintain the ring unit in such precise position until such time as further adjustment is required. Alternatively, a locking mechanism separate from the angular adjustment mechanism may be used to maintain the rotatable ring unit in its adjusted position. The vertical mounting plate 107 has a central opening 125 therein aligned with the openings in the ring units 113, 115. The type of rotational stage 109 shown in the drawings is generally of a type which is commercially available, e.g., Model UTR Series Manual Rotary Stage sold by Newport Corporation of Irvine, Calif.

Figure 6:
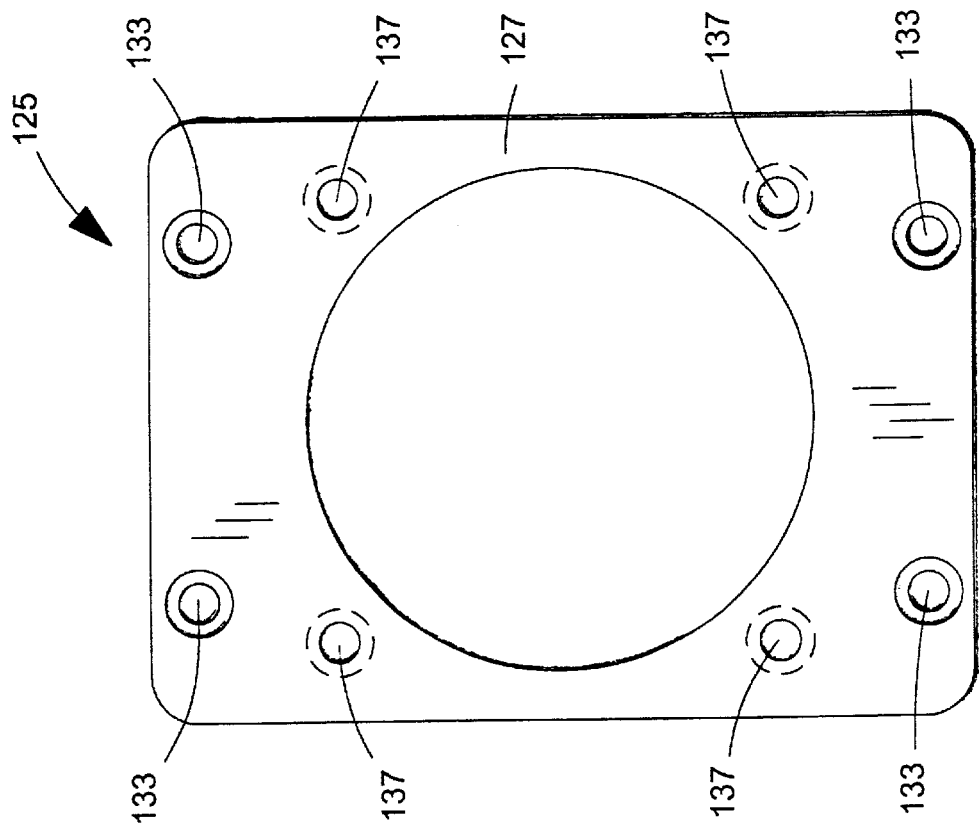
FIG. 6 is a front view of an adaptor plate for mounting the photodetector on the rotational stage.
Figure 7:
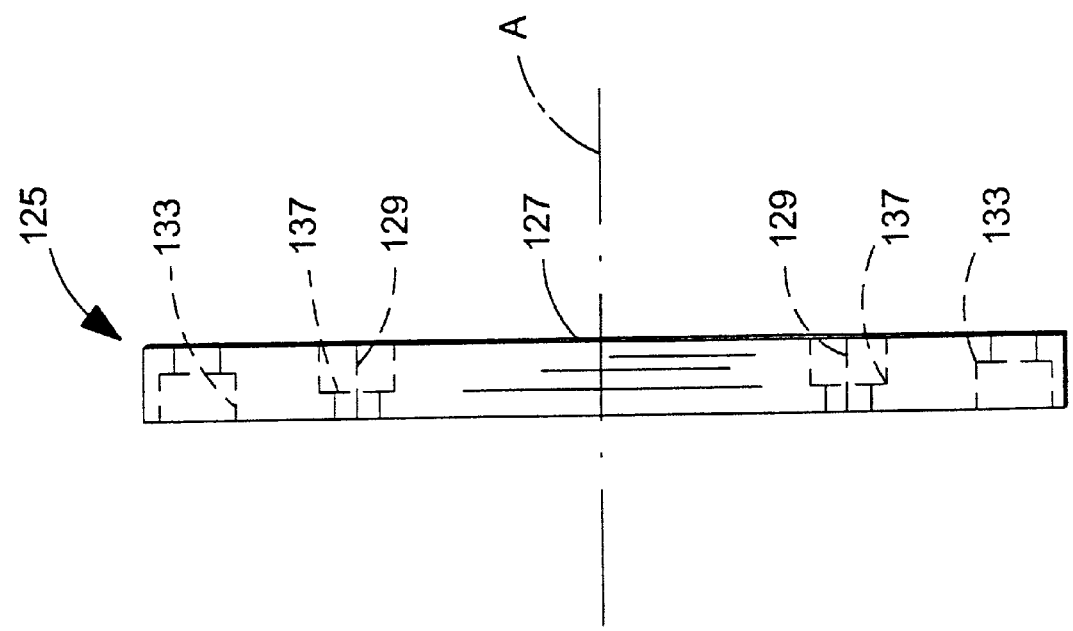
FIG. 7 is a side view of the adaptor plate.

Referring to FIGS. 4, 6 and 7, means generally indicated at 125 is provided for attaching the photodetector 33 to the rotatable ring unit 115 of the rotational stage 109. This means comprises an adaptor, also designated 125, comprising a frame 127 of suitable material (e.g., anodized aluminum) defining an opening 129, fasteners 131 (e.g., screws) receivable in fastener openings 133 in the frame for fastening the adaptor to the front face of the photodetector 33 with the opening 129 in the frame aligned with the linear array 34 of photodetector elements 35, and fasteners 135 (e.g., screws) receivable in fastener openings 137 in the frame for fastening the adaptor to the rear face of the rotatable ring unit 115 of the rotational stage 109 with the frame opening 129 aligned with the opening in the ring unit 115, the openings in the two ring units 113, 115 and the adaptor 125 being sufficiently large to expose the entire linear array 34 of the photodetector 33 to light transmitted by the lens 39. When the photodetector 33 is attached to the rotatable ring unit 115, the unit can be rotated on axis A to adjust the angular orientation of the linear array 34 of photodetector elements 35 relative to the image of the capillary tubes 5 projected by the lens 39 onto the photodetector. Suitable markings (not shown) are provided on the ring units 113, 115 for reading the angular orientation of the rotatable ring unit 115 relative to the stationary ring unit 113. The markings should be sufficiently close together to measure very small increments of rotation (e.g., 1/60 of one degree) to provide very fine adjustment.

Other types of rotational stages and/or mounting assemblies for the photodetector 33 may be used without departing from the scope of this invention. Also, the rotatable ring unit 115 of the rotational stage 109 may be rotatable manually or by a suitable motorized mechanism.

Referring now to FIG. 1, the cooling system 43 of the present invention comprises a thermally insulated enclosure 145 enclosing the bundle 3 of capillary tubes 5, light source 31 and photodetector 33. The cooling system includes a first heat transfer mechanism comprising a conduction heat transfer mechanism, generally designated 151, for cooling the array 23 of closely spaced intermediate portions 21 of the capillary tubes, where the density of the tubes generates a substantial amount of concentrated heat which, unless dissipated, could cause solvent boiling and/or a change in solvent viscosity sufficient to diminish the quality of separation during electrophoresis. The cooling system also includes a second heat transfer mechanism comprising a pair of convective heat transfer units, each generally indicated at 155, for cooling the remaining portions of the bundle, including the inlet end portions 7 and outlet end portions 13 of the tubes 5 which, unlike the array 23, are spread apart and not closely packed.

The enclosure 145 can be in the shape of a large box, having front doors 161 for access to the interior of the enclosure. The enclosure is provided with a layer of thermal insulation 163.

Figure 14:
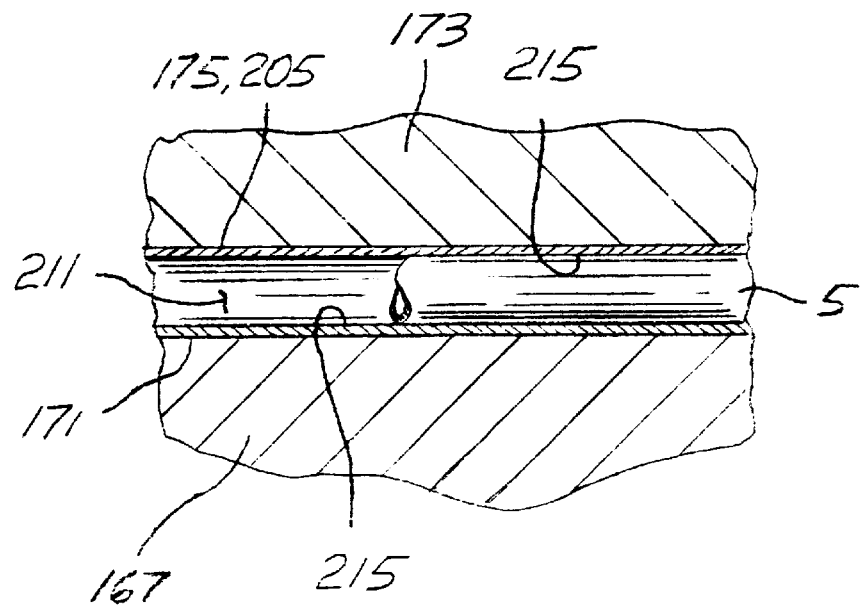
FIG. 14 is an enlarged portion of FIG. 13 showing a capillary tube sandwiched between two slabs of the cooling body, a portion of the tube being removed to show details of construction.
Figure 15:
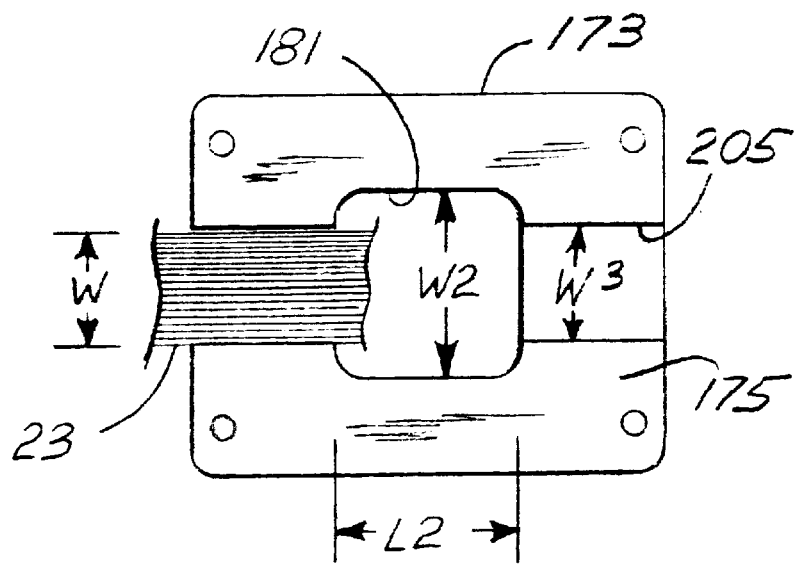
FIG. 15 is a front elevation of a back slab of the cooling body.

In the preferred embodiment shown in FIGS. 2 and 10–15, the conduction heat transfer mechanism 151 comprises a refrigerated body 165 of thermally conductive material (e.g., a metal such as aluminum) having a length L1 and a width W1. The body is supported in the enclosure 145 by a post P and comprises two separate rectangular slabs, i.e., a relatively thick front cooling slab 167 having a front face 169 and a rear face 171, and a thinner back slab 173 having a front face 175 and a rear face 177. The slabs have central aligned window openings 181 therein which combine to form a window, also designated 181, through the body. Referring to FIG. 15, the window 181 has a width W2 greater than the width W of the bundle 3 and a length L2 sufficient to expose the bundle for testing, in this case to permit the passage of light from the light source 31 through the window 181 for incidence on the aforementioned detection window 47 of the capillary bundle 3.

The front slab 167 has passaging therein for the flow of a suitable coolant to cool the slab. (The coolant may be water or other liquid.) This passaging comprises a pair of passages constituted by bores 185, 187 through the slab 167 located on opposite sides of the window 181. The bores 185, 187 are sealingly connected by flexible tubing, as indicated at 191. Bore 187 has an inlet end for connection to a coolant supply line 195 of a suitable refrigeration system 197, and bore 185 has an outlet end for connection to a coolant return line 201 of the same refrigeration system. The refrigeration system 197 may be conventional, such as a Model RTE Series refrigerated bath and recirculating system commercially available from NESLAB Instruments, Inc. of Portsmouth, N.H. This system has a temperature control, including a temperature sensor (not shown) for sensing the temperature of the cooling body 165, so that the temperature of the body can be regulated.

As illustrated best in FIG. 15, the back slab 173 has a channel 205 in its front face 175 which extends the full length L1 of the slab about midway between opposite sides of the slab (the top and bottom sides as shown). When the back slab 173 is attached to the front slab 167, as by fasteners 207, the rear face 171 of the front slab 167 and the walls of the channel 205 combine to define a recess 211 (FIG. 14) which is generally rectangular in horizontal section for receiving the bundle 3 of capillary tubes 5. This recess 211 has a width W3 (FIG. 15) slightly greater than the width W of the bundle 3 at the detection window 47, and a depth (front-to-back direction) which is approximately equal to the diameter of a capillary tube 5 of the bundle, so that the tube is positioned sufficiently close to the rear cooling face 171 of the front slab 167 for the efficient transfer of heat from the tube (and its contents) to the body 165. Preferably, the bundle 3 is in contact with the cooling face 171, but actual contact is not essential so long as sufficient cooling is provided. The recess 211 is positioned relative to the window 181 so that when the bundle 3 is in position, the bundle is aligned with the window so that light transmitted through the window will pass through the capillaries.

The front and back slabs 167, 173 are electrically insulated from the capillary tubes 5 by coatings 215 of a suitable dielectric material (e.g., alumina from an anodizing process) applied at least to the rear face 171 of the front slab 167 and the front face 175 of the back slab 173 (FIG. 14). The coating 215 should be thermally conductive and may have a thickness of 0.5–2.0 mm., for example.

Figure 11:
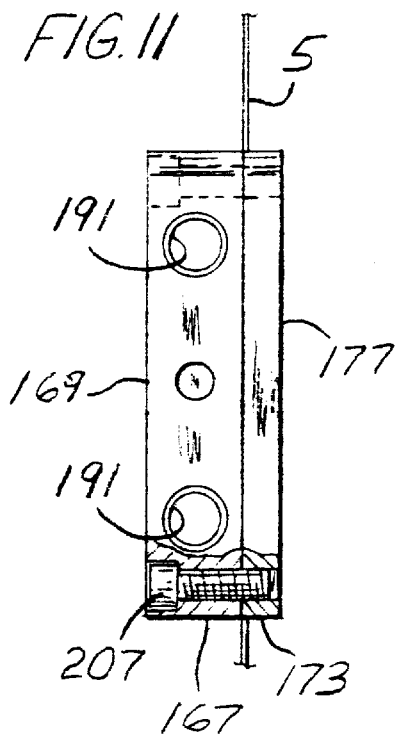
FIG. 11 is a side elevation of the cooling body of FIG. 10.
Figure 12:
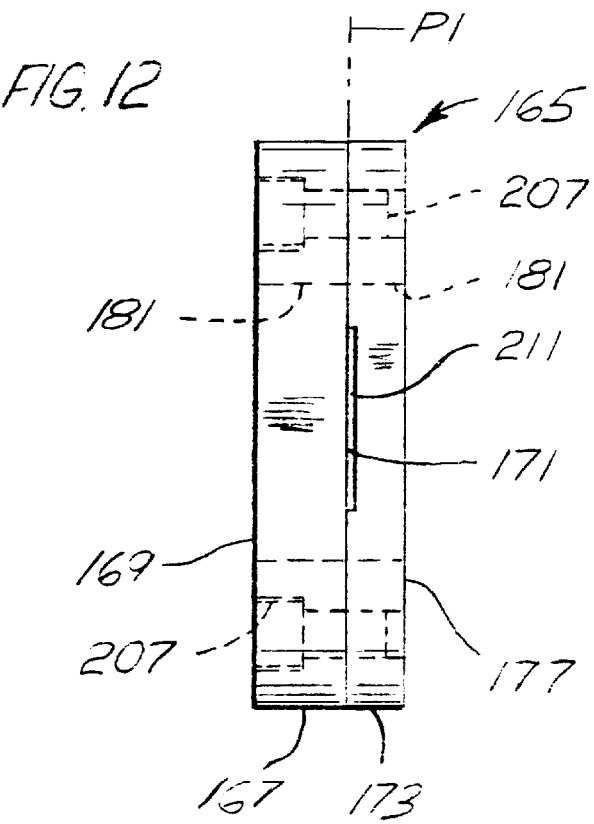
FIG. 12 is a side elevation of the cooling body, with the capillary tubes removed.
Figure 13:
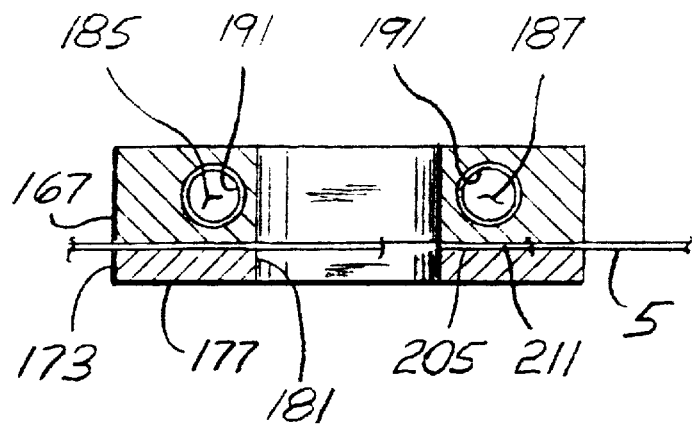
FIG. 13 is vertical section on line 13—13 of FIG. 10.

The fasteners 207 for connecting the two slabs 167, 173, are illustrated in FIG. 11 as bolts received in holes adjacent the four corners of the slabs, the holes in the front slab 167 being non-threaded clearance holes which are counterbored to receive the heads of the bolts, and the holes in the back slab 173 being tapped. Other fastening arrangements may be used.

The slabs 167, 173 may be dimensioned according to the required cooling requirements. Preferably, the slabs have a length L1 sufficient to cover a substantial portion of the length of the bundle 3 (corresponding to the length of the closely spaced array 23) to provide the desired cooling. The slabs 167, 173 should also have a sufficient mass and thermal conductivity to be quickly responsive to temperature adjustments which may be made, as by the aforementioned temperature control of refrigeration system 197.

Other heat transfer mechanisms may be used for cooling the closely spaced array of capillary tubes 5. For example, a thermoelectric device can also be used.

Each convective heat transfer unit 155 comprises a heat exchange device 221 having a cooling surface and a fan 225 for circulating air over the cooling surface and directing such air in an appropriate direction. One of the two units 155 is preferably located adjacent the inlet end portions 7 of the capillary tubes 5 for circulating cool air thereover; the other is preferably located adjacent the photodetector 33, as illustrated in FIG. 1. The two heat exchange devices 221 are operable to maintain the air temperature inside the enclosure in the range of about 0–90 degrees C., preferably in the range of about 0–40 degrees C., and most preferably at about 20 degrees C. Suitable convective heat transfer units of the type described are available, one such unit being available under the trade designation Kodiak Recirculating Chiller— RC022J02BG3 from Lytron Inc. of Woburn, Mass. Other devices may also be used for circulating cooling air inside the enclosure 145 without departing from the scope of this invention.

The conductive and convective heat transfer devices 151, 155 should work together to provide the cooling necessary to prevent overheating of the capillary tubes which, as previously mentioned, can diminish the quality of separation during electrophoresis. The amount of cooling necessary will vary, depending on such factors as the type of buffer (solvent) used, the amount of current and the voltage. In a typical chiral separation electrophoresis operation, for example, the amount of power applied to the bundle will range from about 10–600 watts (1–20 milliamps at 10,000–30,000 volts), generating a corresponding amount of heat in the tubes. Some of this heat will be removed by the conduction heat transfer mechanism 151, and some will be removed by the convective heat transfer units. For example, if the length of the bundle ranges from 50 cm. to 1 meter, the length L1 of the refrigerated body 165 and closely spaced array 23 of tubes is 5–10 cm, and the width W of the bundle at the detection window 47 is about 2.5 cm., the conduction heat transfer mechanism 151 (e.g., body 165) should be capable of dissipating 5%–20% of the heat generated by the current flowing through the bundle, and the convective heat transfer units 155 units should be capable of dissipating the remaining heat generated by such current.

Those of skill in the art will recognize that other capillary dimensions and bundle sizes will generate different amounts of heat. The capillary bundles can have 8 or more capillaries, 16 or more, 24 or more, but more preferably 48 or more and most preferably 96 or more capillaries in the bundle.

Figure 16:
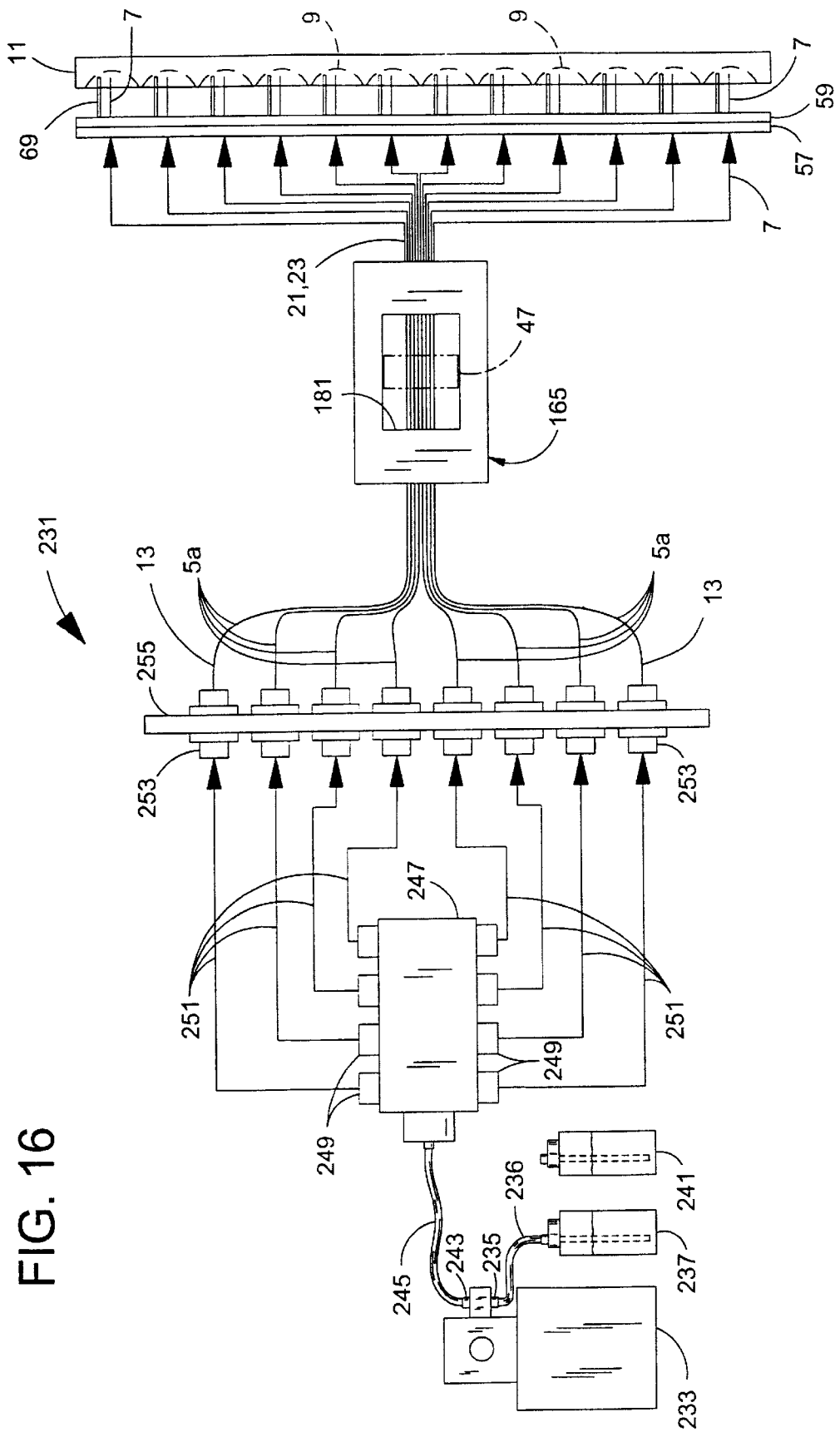
FIG. 16 is a schematic view of a cleaning and buffer loading system.

FIGS. 1 and 16 illustrate a system generally designated 231, for flushing the capillary tubes 5 and also for loading the tubes with a suitable buffer solution prior to conducting an actual sample separation process. The system 231 includes a pump 233 having an inlet 235 for selective connection via a line 236 to a first container 237 containing a supply of flushing solution (e.g., water or an aqueous solution of sodium hydroxide) or to a second container 241 containing a supply of buffer solution (e.g., cyclodextrin for chiral separation). The pump 233 has an outlet 243 connected via line 245 to a manifold 247 having a series of outlet ports 249. Each outlet port 249 is connected to a conduit 251 which extends to one end of a fitting 253 mounted on a support 255 in the enclosure 145, the other end of the fitting being connected to a group 5a of capillary tubes. (For example, a capillary bundle consisting of 96 capillary tubes may be divided into eight groups 5a of 12 tubes each, and each group may be connected to a respective fitting 253.) The arrangement is such that the pump 233 may be operated to pump liquid from the appropriate container 237, 241 for delivery to the capillary tubes 5 via line 245, manifold 247, conduits 251 and fittings 253. The fittings are of conventional design and commercially available, e.g., from Valco Instruments Company, Inc. of Houston, Tex.

In use, the CE system 1 of the present invention is set up as shown in FIG. 1, where the array 23 of the intermediate portions 21 of the parallel capillary tubes 5 lie in a first plane P1 within the channel 205 of the cooling body 165, where the photodetector 33 is mounted on the rotational mount 109 in a position in which the linear array 34 of photodetector elements 35 lies in a second plane P2 generally parallel to the first plane P1, and where the axis of rotation A is generally perpendicular to the two planes P1, P2. (As used herein, "generally parallel" includes an arrangement where the two planes P1, P2 are either exactly parallel or out of parallel with respect to one another by as much as about 15 degrees, and preferably only about 5 degrees. Similarly, "generally perpendicular" includes an arrangement where the axis A is either exactly perpendicular to a plane P1, P2 or off perpendicular by as much as about 7.5 degrees, and preferably only about 2.5 degrees.

The capillary tubes 5 are cleaned ("conditioned") and prepared prior to the start of each sample separation run. This is accomplished by connecting the outlet end portions 13 of groups 5a of the capillary tubes 5 to respective fittings 253 on the support 255, and then operating the pump 233 to pump cleaning solution from the cleaning solution receptacle 237 through the capillary tubes, the flow being in a direction toward the inlet end portions 7 of the tubes. A microtiter plate 11 is positioned on the insulating block 71 to receive cleaning solution as it exits the tubes. After the capillary tubes 5 have been flushed (e.g., "conditioned"), the inlet 235 of the pump 233 is connected to the container 241 containing buffer solution, and the pump is then operated to fill the capillary tubes with buffer solution. After the capillary tubes are properly cleaned and prepared, samples are loaded into the tubes. Sample loading is accomplished by disconnecting the outlet end portions 13 of the capillary tubes from their respective fittings 253 and placing the outlet end portions in the waste receptacle 15. A microtiter plate 11 containing the samples to be analyzed is positioned on the insulating block 71 with the capillary tubes 5 and electrodes 69 extending down into the wells 9 of the plate. The power source is then operated to apply a voltage differential (e.g., 10 kv) across each capillary tube for a period of time (e.g., 10 seconds) suitable to cause the electro-kinetic movement of a quantity of sample from the wells 9 of the microtiter plate 11 into the inlet end portions 7 of the capillary tubes. After samples have been loaded into the capillary tubes, the microtiter plate 11 is replaced by a container of buffer solution so that the inlet end portions 7 of the capillary tubes extend down into the buffer solution. The buffer solution container may be wrapped or otherwise sealed to reduce evaporation of the buffer.

Following sample loading, and prior to the start of an electrophoresis operation, the cooling system 43 is actuated to cool the interior of the enclosure 145 and the capillary tubes 5 therein. This involves actuating the two convective cooling units 155 and also the conduction cooling device 151 for a time sufficient to bring the interior air temperature of the enclosure 145 down to a temperature sufficient to prevent overheating of the capillary tubes and the contents thereof during chiral separation. A temperature in the range of 0–90° C., preferably in the range of 0°–40° C., and most preferably about 20° C., is believed to be suitable for this purpose.

After the enclosure 145 and capillary tubes 5 are suitably cooled, a voltage is applied to the tubes, causing the various components of the samples to migrate at different speeds to effect separation, as will be understood by those skilled in this field. To separate chiral molecules, a relatively large current is required (e.g., a sum total of 750 milliamps for a bundle of 96 capillary tubes), which results in the generation of a substantial amount of heat in the tubes and contents thereof. The conduction heat transfer device 151 removes this heat in the area of the bundle 3 generally adjacent the detection window 47, where the capillary tubes 5 are relatively closely spaced. The convective heat transfer units 155 removes this heat from other portions of the bundle, including the inlet end portions 7 of the tubes 5. As a result, overheating of the capillary tubes and contents thereof is prevented, thus ensuring a more accurate analysis of the samples.

Light from the light source 31 passes through the planar array 23 of the capillary tubes and is projected by the lens 39 as an image of the tubes onto the photodiodes 35 of the photodetector 33. These diodes 35 generate signals which are processed in conventional fashion to generate and display an electropherogram 87 plotting light intensity (indicative of absorption levels) versus time. The clarity, resolution and detection limits of this plot can be improved by rotatably adjusting the rotatable ring unit 115 (carrying the photodetector 33) to find the optimal angular position for providing an electropherogram having better clarity, resolution and/or detection limits. The adjustment procedure is best illustrated in FIGS. 8 and 9.

In FIG. 8, it will be observed that the image of the tubes 5 projected on the linear array 34 of photodiodes is at an angle where the longitudinal centerline 275 of the array is skewed at an angle B relative to the centerline 277 of a tube 5. This orientation does not yield an optimal electropherogram, since the photodiode elements 35 are slanted relative to the lengths of the tubes. The characteristics (clarity, resolution and/or detection limits) of the electropherogram can be improved by rotating the rotatable ring unit 115 of the rotational stage 109, and the photodetector 33 mounted thereon, to the position shown in FIG. 9 where the photodiode elements 35 are more aligned with the projected image of the tubes 5. The optimal angle, indicated at C in FIG. 9, is usually about 90 degrees, that is, an angle where the longitudinal centerline 275 of the linear array 34 of photodetector elements 35 is precisely perpendicular to the capillary tubes (i.e., the projected image of the tubes) and the longitudinal centerlines of the elements 35 are parallel to the longitudinal centerlines 277 of the capillary tubes. The optimal angle is identified by rotating the rotatable ring unit 115 one way or the other until the display of the electropherogram 87, as it appears on the screen 89, is optimal in terms of clarity, resolution and/or detection limits. The ring unit 115 is then maintained in this position throughout the separation process. The precise position of the rotatable ring unit 115 relative to the stationary ring 113 unit can be recorded by using the markings on the two units.

It will be understood from the foregoing that the system described above optimizes the results of a parallel CE operation by improving the clarity, resolution and/or detection limits of electropherograms generated during the separation and analysis process. This is achieved by a method involving rotating the photodetector 33 relative to the projected image of the capillary tubes to a position in which the array 34 of photodetector elements 35 is at an optimal orientation (e.g., as shown in FIG. 9), relative to the image, and then maintaining the photodetector in such position. The optimal orientation is easily determined simply by watching the electropherogram while rotating the photodetector 33 until the display of the electropherogram is optimal.

It will also be observed that the cooling system 43 of this invention will provide efficient well-regulated cooling of the bundle 3 by using the convective and conductive heat transfer devices 151, 155, the conductive device providing additional cooling of the tubes 5 where they are more closely spaced in the area adjacent the window 181 in the body 165 where the samples in the tubes 5 are exposed for CE analysis. Consequently, even during chiral separation and other CE processes generating large amounts of heat, the temperature of the samples will remain well below boiling to avoid the formation of bubbles in the samples which can cause dielectric breakdown, sparking and other undesirable results adversely affecting sample analysis. The system of the present invention can be used for any parallel or multiplexed CE process, including but not limited to the separation of chiral molecules. It is believed that the system described above is the first parallel CE system designed to effect chiral separation.

Chiral separation using parallel CE can be effected with or without the use of circular dichroism ("CD") which is the differential light absorption properties of left and right circularly polarized light and which is a characteristic spectroscopic property of chiral molecules. When CD is used, the throughput can be greatly improved because the separation of enantiomers is not required resulting in a shorter separation/detection times. CD can be used to quantitatively identify enantiomeric excess in the presence of both enantiomers of a chiral species. The system described above can be modified to use CD by placing a photoelastic modulator between the light source 31 and the detection window 47 of the capillary tubes. The modulator modulates the light between the left and right circularly polarized components. The magnitude of the CD signal is determined by taking the difference between the left and right hand signals at the photodetector 33. CD is commonly determined for absorption but can also be determined from a fluorescence signal in a fluorescence detection (rather than light absorption) system. In such a system, an analyte which emits upon illumination (either naturally or via a chemical tag) can be used. In this case, an intense source, lamp or laser, illuminates the capillary array and the resulting emission is detected by the diode array.

While the cooling system of the present system is an important aspect of the present invention, it is contemplated that cooling of the bundle 3 during parallel CE may not be necessary under all circumstances, in which case the cooling devices 151, 155 and/or enclosure 145 may be eliminated.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions and methods without departing from the scope of the invention, it is intended that all matter contained in the above description or shown in the accompanying drawings shall be interpreted as illustrative and not in a limiting sense.

What is claimed is:

1. A multiplexed capillary electrophoresis system comprising:

a bundle of capillary tubes having inlet end portions spaced apart for loading of fluid samples to be analyzed into the tubes, outlet end portions for exit of said fluid samples from the tubes, and intermediate portions between the inlet and outlet end portions arranged in a generally planar array in which the intermediate portions extend side-by-side in closely spaced generally parallel relation, a power source for applying a potential difference between the inlet end portions and the outlet end portions to cause an electrical current to flow through the contents of the capillary tubes at a level sufficient to cause separation in said fluid samples, said current generating heat in the tubes and the contents thereof, a light source for directing light to pass through said array of intermediate portions of the capillary tubes, a photodetector for receiving light passing through said array, a first heat transfer mechanism for cooling said array of closely spaced intermediate portions of the capillary tubes, a second heat transfer mechanism for cooling at least the spaced apart inlet end portions of the capillary tubes, and a thermally insulated enclosure enclosing said bundle of capillary tubes, said light source, said photodetector and said first heat transfer mechanism.

2. A multiplexed capillary electrophoresis system as set forth in claim 1 wherein said first heat transfer mechanism comprises a conduction heat transfer mechanism.

3. A multiplexed capillary electrophoresis system as set forth in claim 2 wherein said array of intermediate portions of the capillary tubes has a width, said conduction heat transfer mechanism comprising a body of thermally conductive material having a length, a width, a cooling face adapted to extend across substantially the entire width of the bundle for cooling the capillaries of the bundle, and a window in the body for exposing said array.

4. A multiplexed capillary electrophoresis system as set forth in claim 3 wherein said conduction heat transfer mechanism further comprises passaging in the body for the flow of a coolant through the body to cool the body, said passaging having an inlet adapted for connection to a source of coolant and an outlet.

5. A multiplexed capillary electrophoresis system as set forth in claim 3 wherein said body has a recess therein extending the length of the body for receiving said array, said cooling face defining one side of said recess.

6. A multiplexed capillary electrophoresis system as set forth in claim 5 wherein said body comprises a front cooling slab having a front face and a rear face constituting said cooling face, and a back slab removably attached to said front cooling slab, said back slab having a front face in contact with the rear face of the front cooling slab and a rear face.

7. A multiplexed capillary electrophoresis system as set forth in claim 6 wherein the front face of the back slab has a shallow channel formed therein defining the remaining sides of the recess in the body, said recess extending completely across the body.

8. A multiplexed capillary electrophoresis system as set forth in claim 7 wherein said window comprises aligned openings in said front and back slabs.

9. A multiplexed capillary electrophoresis system as set forth in claim 3 wherein said body is of metal and said cooling face has a dielectric thermally conductive coating thereon engageable by said capillary tubes.

10. A multiplexed capillary electrophoresis system as set forth in claim 3 further comprising a refrigeration system for controlling the temperature of said body.

11. A multiplexed capillary electrophoresis system as set forth in claim 2 wherein said second heat transfer mechanism comprises a convective heat transfer mechanism.

12. A multiplexed capillary electrophoresis system as set forth in claim 11 wherein said convective heat transfer mechanism comprises a heat exchange device having a cooling surface, and a fan for circulating air over said cooling surface and said inlet end portions of the capillary tubes.

13. A multiplexed capillary electrophoresis system as set forth in claim 12 wherein said heat exchange device and said fan are located in said enclosure.

14. A multiplexed capillary electrophoresis system as set forth in claim 13 wherein said heat exchange device and said fan are operable to maintain the air temperature inside the enclosure in the range of 0–90 degrees C.

15. A multiplexed capillary electrophoresis system as set forth in claim 14 wherein said heat exchange device and said fan are operable to maintain the air temperature inside the enclosure at about 10 degrees C.

16. A multiplexed capillary electrophoresis system as set forth in claim 1 wherein said thermally insulated enclosure encloses said second heat transfer mechanism.

17. A multiplexed capillary electrophoresis system as set forth in claim 1 wherein said fluid samples are chiral fluids, and wherein said power source is operable to cause said electrical current to flow through the fluid samples at a power level sufficient to cause chiral separation.

18. A multiplexed capillary electrophoresis system as set forth in claim 1 wherein said power source is operable to apply 10–600 watts of power to the bundle.

19. A multiplexed capillary electrophoresis system with cooling sufficient to prevent overheating during separation, said system comprising:

a bundle of capillary tubes having inlet end portions spaced apart for loading of fluid samples to be analyzed into the tubes, outlet end portions for exit of said fluid samples from the tubes, and intermediate portions between the inlet and outlet end portions arranged in a generally planar array in which the intermediate portions extend side-by-side in closely spaced generally parallel relation, a power source for applying a potential difference between the inlet end portions and the outlet end portions to cause an electrical current to flow through the contents of the capillary tubes at a level sufficient to cause separation in said fluid samples, said current generating heat in the tubes and the contents thereof, a light source for directing light to pass through said array of intermediate portions of the capillary tubes, a photodetector for receiving light passing through said array, a thermally insulated enclosure enclosing said bundle of capillary tubes, light source and photodetector, a first conduction heat transfer mechanism for cooling said array of closely spaced intermediate portions of the capillary tubes, a second heat transfer mechanism for cooling at least the spaced apart inlet end portions of the capillary tubes, said array of intermediate portions of the capillary tubes having a width, said conduction heat transfer mechanism comprising a body of thermally conductive material having a length, a width, a cooling face adapted to extend across substantially the entire width of the bundle for cooling the capillaries of the bundle, a window in the body for exposing said array, and a dielectric coating on said cooling face.

20. A multiplexed capillary electrophoresis system, said system comprising:

a bundle of capillary tubes having inlet end portions positioned for loading of fluid samples to be analyzed into the tubes, outlet end portions for exit of said samples from the tubes, and intermediate portions between the inlet and outlet end portions arranged in an array in which the intermediate portions extend side-by-side in closely spaced generally parallel relation, a power source for applying a potential difference between the inlet end portions and the outlet end portions to cause an electrical current to flow through the contents of the capillary tubes at a level sufficient to cause separation in said fluid samples, a light source for directing light to pass through said array of intermediate portions of the capillary tubes, a photodetector for receiving light passing through said array, a heat transfer system for cooling said array and said inlet end portions of the capillary tubes to an extent sufficient to prevent overheating of the tubes and contents thereof due to heat generated during separation, and a thermally insulated enclosure enclosing said bundle of capillary tubes, light source, photodetector, and said heat transfer system.

21. A multiplexed capillary electrophoresis system as set forth in claim 20 wherein said heat transfer system comprises a first heat transfer mechanism for cooling said array of closely spaced intermediate portions of the capillary tubes, and a second heat transfer mechanism for cooling at least the inlet end portions of the capillary tubes.

22. A multiplexed capillary electrophoresis system as set forth in claim 21 wherein said first heat transfer mechanism comprises a conduction heat transfer mechanism and said second heat transfer mechanism comprises a convective heat transfer mechanism.

23. A multiplexed capillary electrophoresis system, comprising:

a bundle of capillary tubes having inlet end portions spaced apart for loading of fluid samples to be analyzed into the tubes, outlet end portions for exit of said fluid samples from the tubes, and intermediate portions between the inlet and outlet end portions arranged in an array in which the intermediate portions extend side-by-side in closely spaced generally parallel relation, said array of intermediate portions of the capillary tubes having a width, a power source for applying a potential difference between the inlet end portions and the outlet end portions to cause an electrical current to flow through the contents of the capillary tubes at a level sufficient to cause separation in said fluid samples, said current generating heat in the tubes and the contents thereof, a light source for directing light to pass through said array of intermediate portions of the capillary tubes, a photodetector for receiving light passing through said array, a thermally insulated enclosure enclosing said bundle of capillary tubes, light source and photodetector, a conduction heat transfer mechanism for cooling said array of closely spaced intermediate portions of the capillary tubes, said conduction heat transfer mechanism comprising a body of thermally conductive material having a length, a width, a cooling face adapted to extend across substantially the entire width of the bundle for cooling the capillaries of the bundle, said cooling face being electrically insulated from said capillaries, and a window in the body for exposing said array.

* * * * *